United States Patent
Mooney

(10) Patent No.: US 7,552,133 B1
(45) Date of Patent: Jun. 23, 2009

(54) METHOD OF SUPPLYING AND DISPENSING PRESCRIBED MEDICAL SUPPLIES THROUGH A WEB SITE ASSOCIATED WITH A MEDICAL CARE PROVIDER

(76) Inventor: Al J. Mooney, 509 Mildenhall Way, Cary, NC (US) 27513

( * ) Notice: Subject to any disclaimer, the term of this patent is extended or adjusted under 35 U.S.C. 154(b) by 1706 days.

(21) Appl. No.: 09/492,398

(22) Filed: Jan. 27, 2000

(51) Int. Cl.
*G06F 17/00* (2006.01)
(52) U.S. Cl. .................... 707/102; 707/100; 707/101
(58) Field of Classification Search .............. 705/2, 705/3, 4; 700/236; 600/300, 301; 707/100–102
See application file for complete search history.

(56) References Cited

U.S. PATENT DOCUMENTS

| | | | |
|---|---|---|---|
| 5,619,991 A | 4/1997 | Sloane | |
| 5,842,976 A * | 12/1998 | Williamson | 600/300 |
| 5,845,255 A | 12/1998 | Mayaud | |
| 6,047,259 A * | 4/2000 | Campbell et al. | 705/3 |
| 6,068,156 A * | 5/2000 | Liff et al. | 705/2 |
| 6,088,429 A | 7/2000 | Garcia | |
| 6,269,339 B1 * | 7/2001 | Silver | 705/2 |

OTHER PUBLICATIONS

US Code Collection, Title 42, Section 1320a-7b, obtained from Internet at www.law.cornell.edu, Apr. 3, 2003.*
"Federal Anti-Kickback Law and REgulatory Safe Harbors", published by Social Security Administration, Office of Inspector General, Nov. 1999.*

* cited by examiner

*Primary Examiner*—Sana Al-Hashemi
(74) *Attorney, Agent, or Firm*—Coats & Bennett, P.L.L.C.

(57) ABSTRACT

A medical care provider provides a network gateway with descriptions of frequently prescribed medical devices thereon. A patient may access the gateway and use the gateway to facilitate the purchase of a prescribed medical device. The gateway communicates through an e-commerce provider to a medical supply vendor to arrange for the shipping of the purchased medical device and arrange for payment thereto.

15 Claims, 3 Drawing Sheets

METHOD OF SUPPLYING AND DISPENSING PRESCRIBED MEDICAL SUPPLIES THROUGH A WEB SITE ASSOCIATED WITH A MEDICAL CARE PROVIDER

BACKGROUND OF THE INVENTION

1. Field of the Invention

The present invention relates to a system and method of prescribing and delivering medical supplies through an Internet web site associated with the prescribing medical care provider.

2. Description of the Related Art

Physicians are continuously confronted with patients who need medical supplies as part of a treatment associated with their illness or condition. These may be walkers, slings, special splints, or the like. These devices can be fairly specialized, not particularly inexpensive and somewhat hard to find in your average drug store. In large communities or cities, a specialty store may exist allowing the in-store purchase of such supplies without too much inconvenience to the patient. However, in smaller communities, patients may find it extremely difficult to locate a specialized supply that a doctor has told them that they need. This may be especially true in situations where the patient has limited mobility or poor access to transportation.

In the present, the patient must scrounge the means to locate and travel to the specialty store, only to be told potentially that the item in question must be ordered from a manufacturer, adding delay to time before the patient receives the item in question.

The Internet and its proliferating web pages may facilitate some commerce in the medical industry. However, there remains a dearth of companies that provide medical supplies for sale over the Internet. Even where such companies do exist, patients may have a difficult time locating the appropriate web site. Further, even when the right web site is located, the medicalese language used on the web site may make it difficult for the patient to locate the object best suited for his needs. Still further, not every patient may have access to the Internet, or be computer savvy enough to navigate even the simplest of web sites.

In short, there remains a need for a user friendly web site that allows e-commerce to take place in the field of medical supplies, and particularly one that is managed by the prescribing physician to ensure that appropriate supplies are available for selection by patients, and that the site is tailored to the level of sophistication of the patients with which the particular managing physician deals.

SUMMARY OF THE INVENTION

A physician or other approved medical care provider is well suited to solve the problems in the prior art. The medical care provider initially creates a network gateway, such as a web page on the Internet. The web page lists at a minimum a number of medical supplies that the provider is likely to prescribe to patients. In the preferred embodiment, photos of the supplies, detailed descriptions of the supplies, and instructions on the use of the supplies are also present. Further, if the supplies are available in a plurality of sizes, the various sizes and models are detailed in similar fashion. The gateway acts as a platform from which a viewer may make a purchase of a desired supply as is explained in greater detail below.

The medical care provider prescribes a medical supply to a patient as a result of an appropriate consultation. Knowing what is available on the gateway, the provider may explicitly identify the make, model and size that the patient requires with confidence that it is available on the gateway. The patient may access the gateway from a computer, such as one located in the patient's home or in the provider's office and select the appropriate prescribed item or supply. The gateway communicates this selection to an appropriate medical supply vendor, preferably through an e-commerce provider who accepts payment information from the patient. Payment may initially be made to the e-commerce provider, the medical supply vendor, or the provider's account. The medical supply vendor ships the product to the patient and the financial side of the transaction is sorted out in due course such that the vendor is paid, the e-commerce provider is paid and the medical care provider is paid. The patient then has the supply without having to travel to a specialty store or worry about whether the item will be in stock. Rather the product is delivered to the patient's address by suitable courier.

Other objects and advantages of the present invention will become apparent and obvious from a study of the following description and the accompanying drawings which are merely illustrative of such invention.

DETAILED DESCRIPTION OF THE PREFERRED EMBODIMENTS

The present invention provides a technique for a medical care provider to assist his or her patients is purchasing and securing the proper medical supply for treatment. The disclosure will speak in terms of the medical care provider being a doctor, but it should be appreciated that other medical professionals such as nurse practitioners, physician assistants, chiropractors, or the like may all fall under the title medical care provider. As used herein, the term "medical supply" includes pharmaceutical products as well as more traditional medical devices. As used herein, the term "medical device" includes the class of products such as crutches, slings, splints, bandages, walkers, prostheses, and the like. This list is intended to be exemplary and not limiting with respect to the items that fall within the definition of the term "medical device." Further, as used herein "prescribe" shall be interpreted as "to designate or order the use of as a remedy."

Figure 1:
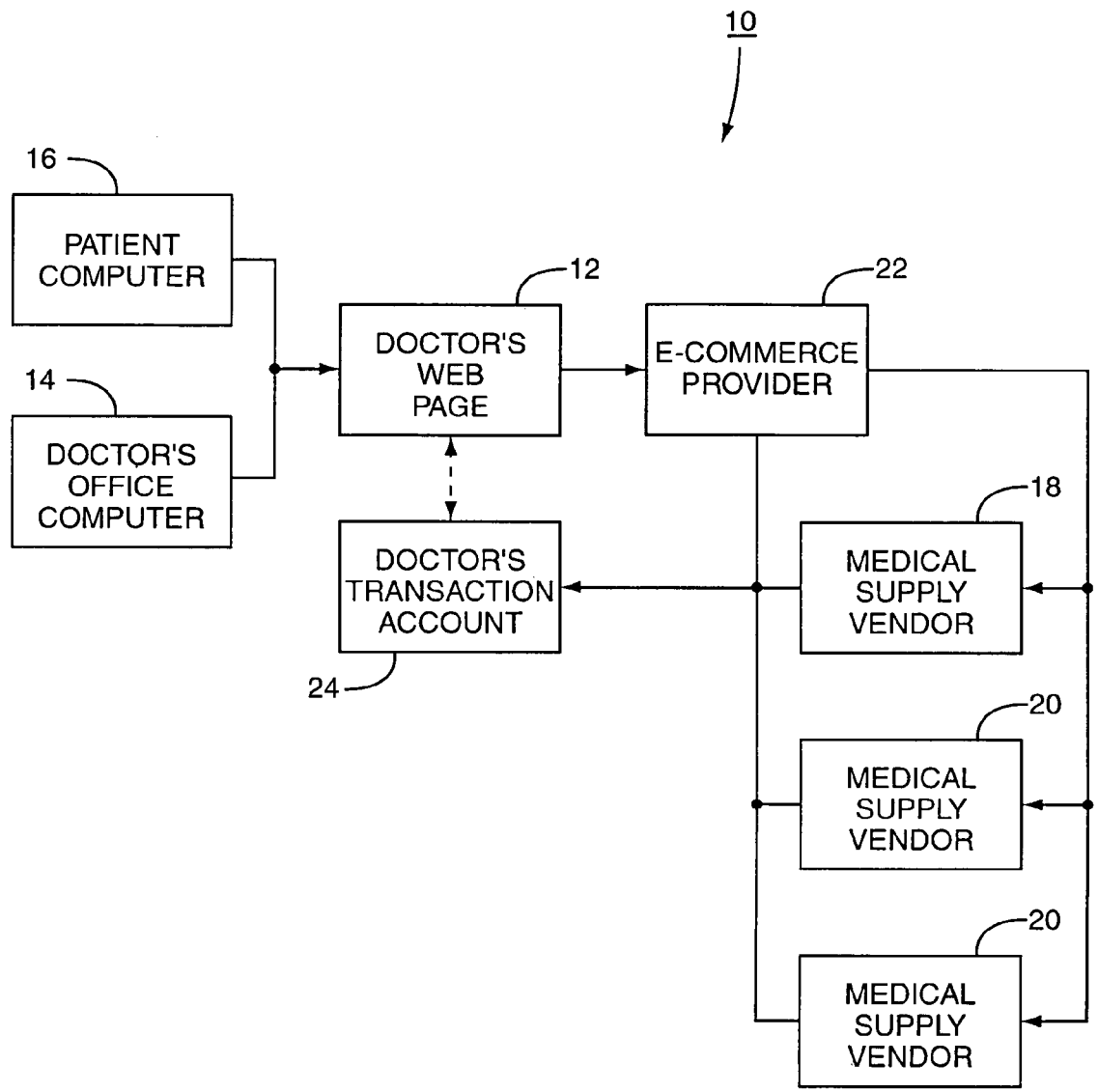
FIG. 1 is a block diagram of the network of the present invention.

As shown in FIG. 1, this technique is facilitated by a system 10 formed from a plurality of computers. Specifically, the doctor establishes a web page 12, that is viewable from a computer such as a doctor's office computer 14, and preferably also from a patient's computer 16. The web page 12 communicates with at least one medical supply vendor computer 18. Additional medical supply vendor computers 20 may be communicated with as needed or desired. The communication with the medical supply vendor computers 18 and 20 preferably takes place through an e-commerce provider 22. Additionally, the computers should have the appropriate financial record keeping ability to track purchases, accept payment, credit, and debit the appropriate accounts. Of particular interest for the medical care provider is the doctor's transaction account 24, but it should be understood that the e-commerce provider 22 and the medical supply vendors also have transaction accounts.

The preferred implementation of the present invention is that the doctor's web page 12 be created with a hypertext language such as HTML, SGML, HDML or XML and that the computers are interconnected by the Internet. Communication therebetween may take place via e-mail or other standard communication formats as is well known in the computer industry. Where financial information such as a credit card number is being transmitted, appropriate encryption or other security measures may be put in place to ensure that the sensitive financial information is not stolen. However, the interconnection could take place over a dedicated network. While feasible, such dedicated networks are relatively expensive, and the volume of communication may not justify such an investment. Furthermore, the use of a dedicated network may inhibit the ability of the patient to access the doctor's web page 12 from the patient computer 16 unless the doctor's web page 12 has an external phone line and allows patients to log in through a modem or other equivalent technique. It is preferred that the doctor's computer 14 acts as the server for the web page 12, but this is not required. Instead, a second host computer may act as the server for the web page 12 and the doctor's computer 14 merely access the host as needed. It should be appreciated that while the preferred embodiment of the present invention works through an e-commerce provider, it is possible to implement the functionality into the computer hosting the doctor's web page 12.

Figure 3A:
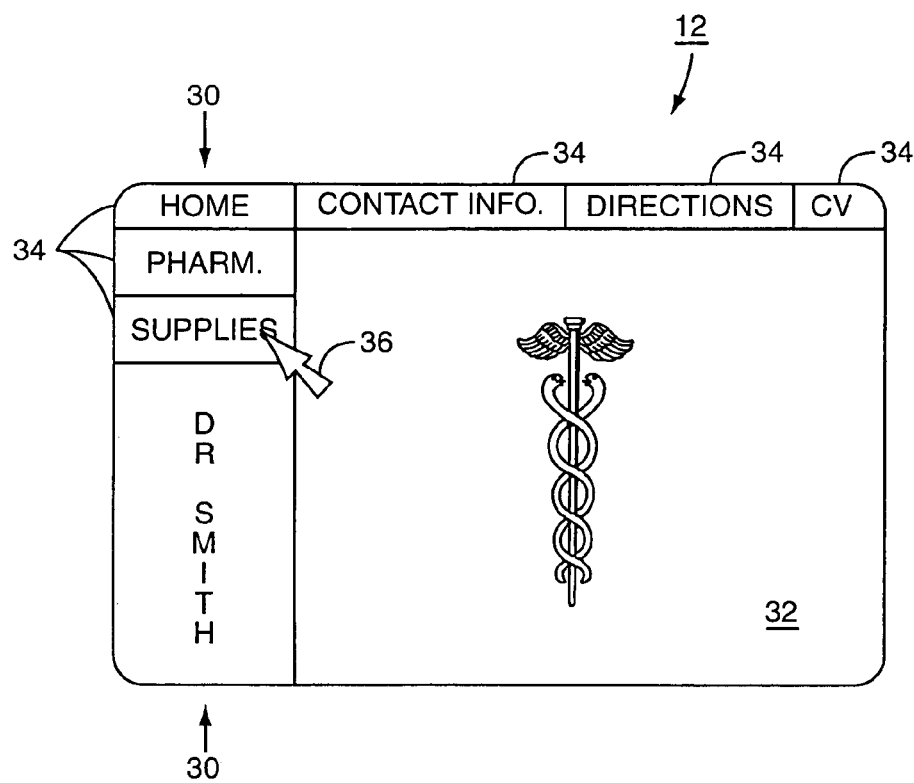
FIGS. 3A and 3B show exemplary medical care provider web pages of the type that might be used to carry out the present invention.
Figure 3B:
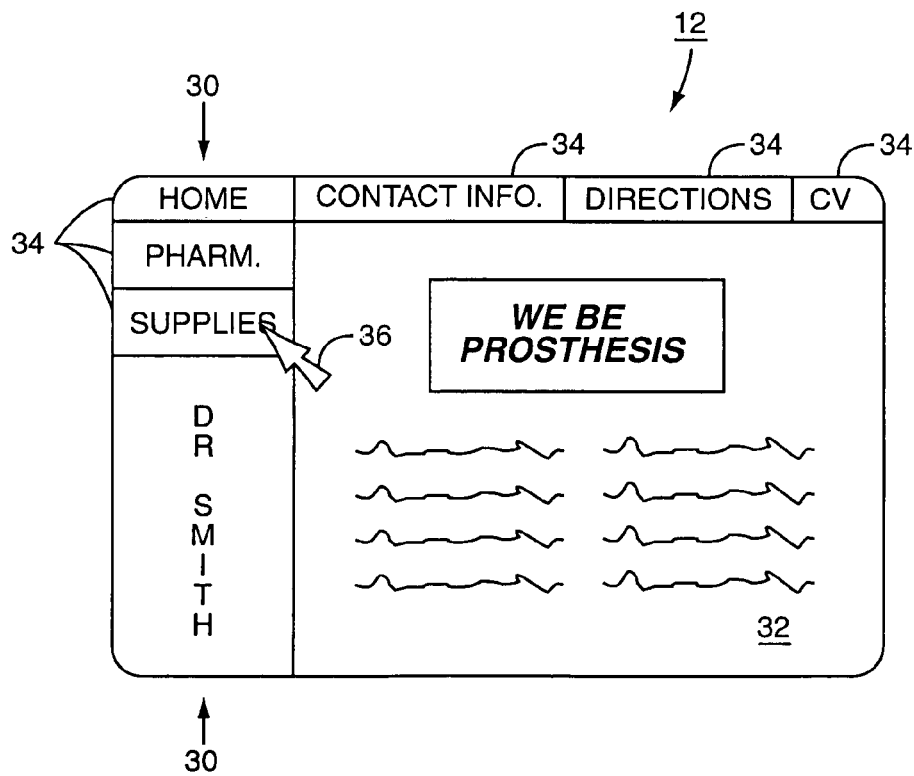

An exemplary web page 12 is seen in FIG. 3. Web page 12 acts as a network gateway and includes a static frame 30 and an active frame 32. The static frame 30 may include a number of links 34 that are activatable by a cursor 36. Example links may include the curricula vitae of the doctor, directions to the office, contact information, a "home" link, a pharmacy link, and a "SUPPLIES" link. Further, it is expected that the medical care provider will use the web page to educate and inform his patients and thus there may be provided links to other medical web sites of interest, a Frequently Asked Question (FAQ) page, medical periodicals, or the like. These may be related to research that the medical care provider is involved in, interested in, or otherwise feels may be helpful to his patients. Activation of a link 34 in the static frame 30 may change the display in active frame 32. In fact, web pages from remote computers may be opened within active frame 32 without changing static frame 30. Thus, upon initially accessing the doctor's web page 12, version A may be seen. After clicking on link 38 to "SUPPLIES" version B may be seen wherein the active frame 32 now displays a web page from one of the medical supply vendor computers 18 or 20. It should be appreciated that while only one "SUPPLIES" link 38 is shown, a plurality of such links, with more specific appellations like prostheses, slings, splints, etc., may also be provided. Alternatively, a single "SUPPLIES" link 38 may take the user to an intermediate page that has a number of different vendors listed.

Further, the "SUPPLIES" link 38 may be merged with the "PHARMACY" link in keeping with the definition of medical supply. While the regulations surrounding the on-line purchase of pharmaceutical products continues to evolve, it is expected that this commercial activity will be allowed in some form. Therefore, the present invention is designed to allow the purchase of pharmaceutical products as well as other medical devices. Pharmaceutical distributors or suppliers may be viewed as medical supply vendors as used herein.

Figure 2:
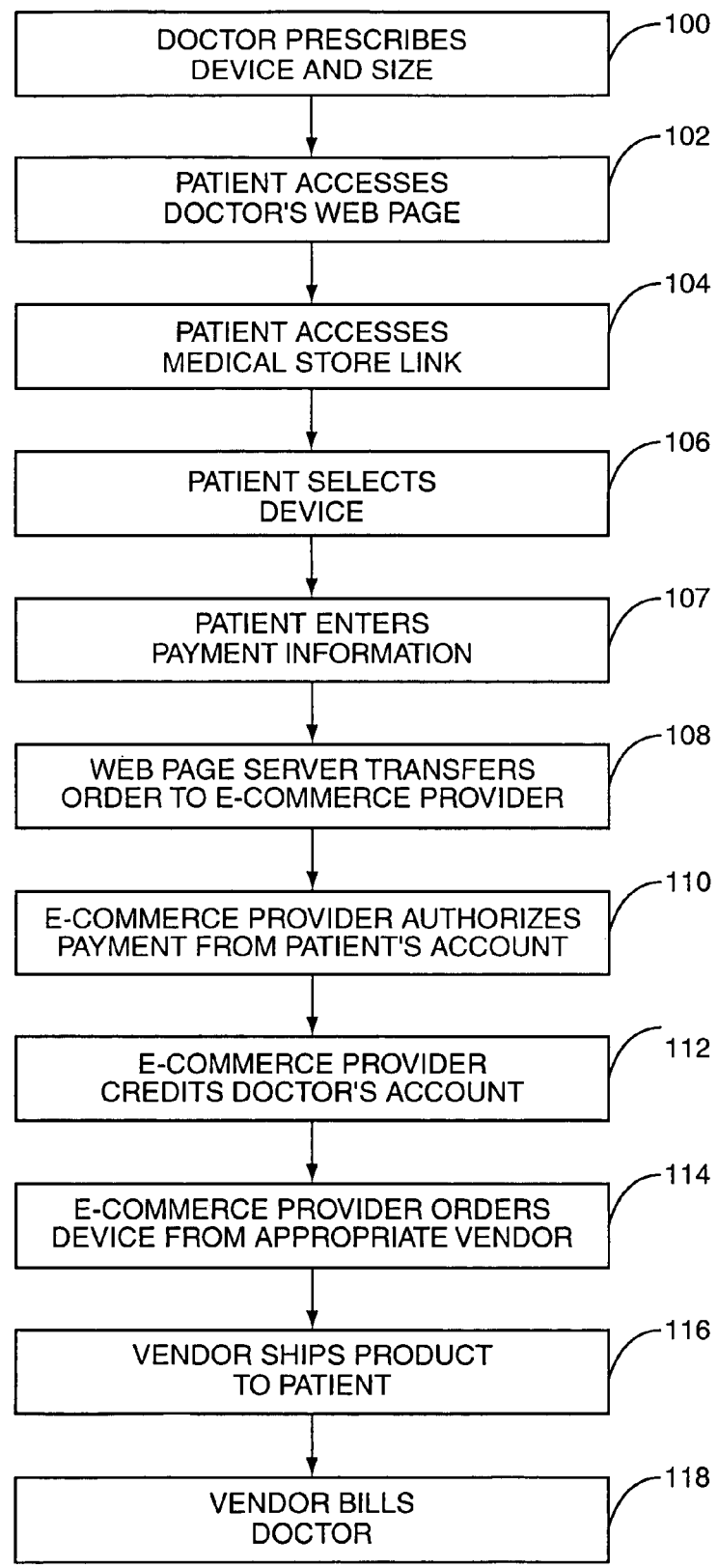
FIG. 2 is a flow chart of the method of the present invention.

With the system 10 provided, the medical care provider is then able to help his patients find and purchase the proper medical supply. The preferred method is seen in flow chart form in FIG. 2. Specifically, the doctor performs a typical consultation and prescribes a particular medical supply, and where appropriate a specific size (block 100). Because the doctor is familiar with the links 34 on the web page 12, the doctor may provide more precise information about the nature of the supply needed, confident in the knowledge that the exact supply is available through the web page 12. The patient may then access the doctor's web page 12, either from his computer 16 or from the doctor's computer 14 (block 102). The patient, armed with the doctor's order, may then click on the "SUPPLIES" link (block 104). In one embodiment, each medical supply vendor computer 18 or 20 has its own web page with products available listed thereon. These vendor web pages are opened in the active display 32 for perusal by the patient. In another embodiment, all the product information is part of the doctor's web page. In either case, the patient may select the supply that the doctor prescribed (block 106). The patient is then prompted for payment information. E-commerce is becoming more prevalent, and techniques to ensure privacy, pop-up screens for credit card information entry, and the like are increasingly well known, and will not be discussed further. Regardless of the particular implementation, the patient enters payment information (block 107).

The doctor's web page, and more particularly the computer serving as the host to the web page sends the order to the e-commerce provider 22 (block 108). The e-commerce provider then authorizes payment from the patient's account (block 110). For example, if the patient has tendered payment with a credit card number, the e-commerce provider could contact the credit card company hosting the account and secure payment therefrom. This process is well understood in the art and will not be further discussed.

In a first aspect of the invention, the e-commerce provider 22 credits the doctor's transaction account 24 (block 112), and places the appropriate order with the medical supply vendor (block 114). The vendor then ships the product to the patient (block 116), and the vendor then bills the doctor (block 118). The e-commerce provider 22 takes a transaction fee and everyone gets paid. As would be understood, the shipping is preferably performed by a common carrier such as FEDERAL EXPRESS®, AIRBORNE EXPRESS®, UPS®, local courier or the United States Postal Service.

In a second aspect of the invention, the e-commerce provider 22 credits the vendor's transaction account, while holding back a transaction fee, and places the appropriate order (block 114). The vendor ships the product (block 116) and the vendor directs a referral fee to the doctor's transaction account.

In a third aspect of the invention, wherein the e-commerce provider is integrated into the doctor's web page 12, the doctor's account 24 is credited immediately, and the web page host computer orders the device from the vendor (block 114). After the vendor ships the product (block 116), the doctor's account 24 credits the vendors account or the vendor bills the doctor's account 24 (block 118).

Other variations of arranging payment between the parties is also well within the scope of the present invention. The present invention offers solutions heretofore unavailable to patients and medical care providers in that the medical care provider has direct knowledge of what products are available on his web page 12, and thus can tailor prescriptions to make sure that the appropriate product is available for purchase by the patient. Additionally, the patient is better served in that he or she gets the supply needed, without having to travel to a specialty store. Overnight delivery ensures that the product arrives in a timely fashion.

Additionally, the medical care provider may walk the patient through the ordering process on the doctor's computer 14. Thus, the medical care provider may go through the links until the desired medical supply is located and then allow the patient to complete the financial side of the transaction as previously described.

The present contemplates providing or ordering medical supplies through an e-commerce format that revolves around a medical doctor or other licensed medical care provider. In particular, the doctor or licensed medical provider will examine a patient and make a diagnosis based on such examinations. Thereafter the doctor or licensed medical care provider will make decisions based on the examination and diagnosis made and thereafter will order appropriate medical supplies that can be procured by the patient or the doctor through the e-commerce format disclosed herein.

The present invention may, of course, be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method of prescribing and selling a medical supply through a website associated with a medical care provider comprising:
    conducting a medical examination on a patient, wherein the medical examination is conducted by the medical care provider;
    prescribing the medical supply for the patient, wherein the medical supply is prescribed by the medical care provider based on the results of the medical examination;
    accessing the website hosted by a server associated with the medical care provider from a client computing device via a communication network, wherein the website includes an array of prescription medical supplies including the medical supply prescribed by the medical care provider;
    displaying the array of prescription medical supplies on a display connected to the client computing device;
    identifying the prescribed medical supply by activating one or more links displayed on the display;
    ordering the medical supply prescribed by the medical care provider from the website associated with the medical care provider by ordering the medical supply from a medical supply vendor that fulfills the electronic order placed through the website associated with the medical care provider, wherein the medical supply vendor is a supplier of medical devices;
    submitting an electronic payment from the client computing device through an e-commerce provider to pay for the prescribed medical supply; and
    electronically routing an electronic payment to the medical care provider that prescribed the medical supply for the medical supply ordered from the website associated with the medical care provider.

2. The method of claim 1 wherein the medical supply vendor is a supplier of pharmaceutical products.

3. The method of claim 1 wherein the medical supply vendor is the medical care provider.

4. The method of claim 1 wherein the e-commerce provider credits or debits an account associated with the medical supply vendor for the sale of the medical supply prescribed by the medical care provider.

5. The method of claim 4 wherein the e-commerce provider is the medical care provider.

6. The method of claim 1 wherein the e-commerce provider credits or debits an account associated with the medical care provider that prescribed the medical supply for the sale of the medical supply.

7. The method of claim 6 wherein the e-commerce provider is the medical supply vendor.

8. The method of claim 1 wherein the e-commerce provider credits or debits an account associated with the medical supply vendor and an account associated with the medical care provider for the sale of the medical supply prescribed by the medical care provider.

9. The method of claim 1 wherein the medical care provider is a licensed medical care professional.

10. A method of prescribing and selling a medical supply through a website associated with a medical care provider comprising:
    conducting a medical examination on a patient, wherein the medical examination is conducted by a medical care provider having a website;
    prescribing a medical supply for the patient, wherein the medical supply is prescribed by the medical care provider based on the results of the medical examination;
    via a communication network, providing access from a client computing device having a display to a computer server hosting the website associated with the medical care provider, wherein the website includes an array of prescription medical supplies including the medical supply prescribed by the medical care provider for display to a user operating the client computing device;
    receiving, at the server hosting the website associated with the medical care provider, an electronic order for the medical supply; and
    receiving an electronically routed electronic payment for the medical supply ordered from the website associated with the medical care provider.

11. The method of claim 10 further comprising arranging the electronic payment through an e-commerce provider for the medical supply prescribed by the medical care provider.

12. The method of claim 11 wherein the e-commerce provider electronically credits or debits an account associated with the medical care provider that prescribed the medical supply for the sale of the medical supply.

13. The method of claim 11 wherein the e-commerce provider is the medical care provider.

14. The method of claim 10 wherein the medical care provider is a licensed medical care professional.

15. The method of claim 10 wherein providing access to the website associated with the medical care provider comprises maintaining a website on the World Wide Web.

\* \* \* \* \*